United States Patent [19]

Booker et al.

[11] Patent Number: 4,503,255

[45] Date of Patent: Mar. 5, 1985

[54] PROCESS FOR RECOVERING TRIARYLPHOSPHINE FROM POISONED RHODIUM CATALYST SYSTEMS

[75] Inventors: David F. Booker, Royston; David E. Grove, Cambridge, both of England; Phillip J. Cotterill, Greenfield; Robert G. Tyson, Prestatyn, both of Wales

[73] Assignee: Johnson Matthey Public Limited Company, London, England

[21] Appl. No.: 373,176

[22] Filed: Apr. 29, 1982

[30] Foreign Application Priority Data

May 1, 1981 [GB] United Kingdom ............... 8113503

[51] Int. Cl.$^3$ .............................................. C07F 9/50
[52] U.S. Cl. ................................. 568/17; 260/429 R; 568/454
[58] Field of Search ............. 260/429 R; 568/17, 454

[56] References Cited

U.S. PATENT DOCUMENTS

| | | | |
|---|---|---|---|
| 3,527,809 | 9/1970 | Pruett et al. ......................... | 568/454 |
| 3,547,964 | 12/1970 | Olivier ............................ | 260/429 R |
| 3,560,539 | 2/1971 | Booth ............................. | 260/429 R |
| 3,968,134 | 7/1976 | Gregorio et al. ............... | 260/429 R |
| 4,009,003 | 2/1977 | Stautzenberger et al. ....... | 568/17 X |
| 4,113,754 | 9/1978 | Kummer et al. ................ | 260/429 R |
| 4,283,304 | 8/1981 | Bryant et al. .................... | 568/17 X |
| 4,374,278 | 2/1983 | Bryant et al. ................... | 260/429 R |

FOREIGN PATENT DOCUMENTS

| | | | |
|---|---|---|---|
| 17183 | 10/1980 | European Pat. Off. | |
| 2048862 | 12/1980 | United Kingdom. | |
| 2074166 | 10/1981 | United Kingdom ................. | 568/17 |

*Primary Examiner*—Helen M. S. Sneed
*Attorney, Agent, or Firm*—Cushman, Darby & Cushman

[57] ABSTRACT

A process for recovering re-usable triarylphosphine (e.g. triphenylphosphine) from rhodium catalyst residues poisoned by the presence of alkyldiarylphosphine (e.g. n-propyldiphenylphosphine) such as are obtained as spent catalyst residues from the hydroformylation of olefins. The process comprises subjecting the poisoned residues to evaporative separation under reduced pressure to separate a vapor comprising triarylphosphine from the rhodium and then mixing the condensed vapor with polar solvent and obtaining the triarylphosphine as a crystalline precipitate from the solvent. The crystalline phosphine is sufficiently free of poisons to be re-usable as a catalyst component in a hydroformylation process.

9 Claims, No Drawings

PROCESS FOR RECOVERING TRIARYLPHOSPHINE FROM POISONED RHODIUM CATALYST SYSTEMS

This invention relates to a process for recovering triarylphosphine from a poisoned rhodium catalyst system comprising rhodium moiety, triarylphosphine and poisonous alkyldiarylphosphine.

Catalyst systems comprising rhodium moiety and triarylphosphine are used in the hydroformylation of olefins, but as the hyroformylation reaction proceeds, poison including mixed poisonous alkylarylphosphine is slowly generated and eventually the poisoned catalyst system has to be removed and replaced by a fresh system. In present commercial practice, the very valuable rhodium moiety is extracted from the poisoned system and subsequently re-used but the contaminated triarylphosphine has to be discarded. Discarding the phosphine represents a loss of an expensive fine chemical and also creates a pollution problem. Clearly a process which could recover the triarylphosphine in a re-usable state would not only reduce costs but would also reduce the pollution problem.

European patent specification 0 017 183 published in October 1980 describes an evaporative technique (for example conventional vacuum distillation or preferably vacuum distillation by means of thin-film or wiped-film evaporators) for removing a mixture of comparatively volatile materials including triarylphosphine from rhodium catalyst systems taken from a hydroformylation process. The primary objective of EP 0 017 183 is to recover the rhodium moiety in a readily re-usable state but it also discloses that the mixture of volatile materials may also be re-used as an impure form of triarylphosphine provided that the mixture does not contain impurities which have a adverse effect on the activity or selectivity of the catalyst system. EP 0 017 183 mentions that the poisonous alkyldiarylphosphines can be removed from hydroformylation catalyst systems by treatment with maleic acid or maleic anhydride. They may also be removed by sophisticated fractionation techniques but such techniques require highly skilful operation.

British patent specification 2,048,862A published in December 1980 discloses the use of crystallisation techniques for the recovery of triarylphosphine from catalyst systems taken from a hydroformylation process. After being taken from the hydroformylation process, the catalyst system is first subjected to a mild distillation to remove very volatile materials such as toluene and then the distillation residue comprising rhodium moiety and triarylphosphine is cooled to cause separation of the phosphine by crystallisation. The primary objective of GB Pat. No. 2,048,862A is to cleanse the triarylphosphine of phosphine oxides and hence its process is not performed on spent catalyst systems where a significant amount of alkyldiarylphosphine has been formed.

An object of this invention is to provide a process for recovering re-usable triarylphosphines from rhodium catalyst systems which contain as much as 0.1% by weight of alkyldiarylphosphine.

Accordingly this invention provides a process for recovering triarylphosphine from a poisoned rhodium catalyst system comprising components which include rhodium moiety, triarylphosphine (preferably triphenylphosphine) and poison, the process comprising separating components by evaporative and crystallisation techniques wherein the poison comprises a poisonous amount (usually 0.1 to 3% by weight) of alkyldiarylphosphine and wherein the process also comprises:

(a) subjecting the poisoned catalyst system to conditions of temperature and pressure (preferably 150° to 220° C. and pressures below 0.001 MN/m$^2$) which cause evaporative separation from the rhodium moiety of a vapour comprising triarylphosphine and then condensing the vapour, (b) subjecting the condensed vapour to a further but milder evaporative process which causes evaporation of at least some material which is more volatile than triarylphosphine so producing a concentrate of triarylphosphine and then (c) mixing the concentrate with a polar solvent, cooling the mixture to a temperature (preferably −10° to 35° C. and usually −5° to 15° C.) at which the triarylphosphine crystallises from the remainder of the mixture and recovering the crystallised triarylphosphine by physical separation (for example filtration) from the remainder of the mixture.

This process enables triarylphosphines recovered from catalyst systems poisoned by 0.1% by weight or more of alkyldiarylphosphine (especially propyldiphenylphosphine or butyldiphenylphosphine) to be used as a component of a rhodium catalyst system in a hydroformylation process.

The milder evaporative separation process of step (b) above may be performed at temperatures of for example 100° to 200° C. (preferably 120° to 170° C.) and pressures of for example 0.0005 to 0.01 MN/m$^2$ (preferably 0.001 to 0.003 MN/m$^2$) always provided that the combination of temperature and pressure chosen produces an evaporative separation which is milder than that performed in step (a) so as to avoid loss of significant amounts of triarylphosphine by evaporation. Preferably step (b) is repeated from one to six times to obtain a highly concentrated concentrate for use in step (c).

The polar solvent with which the condensed vapour is mixed is preferably non-acidic and miscible with water. Especially suitable solvents are short chain (ie containing 1 to 6 carbon atoms) alcohols, for example methanol, ethanol or isopropanol. Optionally the alcohols may be mixed with water although it is preferred that not more than 25 mls of water be added to each 100 mls of alcohol to make an alcohol/water mixture.

To cause crystallisation, the mixture of condensed vapour and polar solvent is cooled and held at the cooled temperature for preferably 1 to 24 hours and usually for 5 to 18 hours. Crystallised triarylphossphine is easily recovered by filtration, centrifugation or sedimentation. The purity of the recovered triarylphosphine usually exceeds 83% by weight. When the polar solvent is non-acidic and miscible with water, higher purities can be conveniently achieved by agitating the recovered triarylphosphine with fresh solvent whereupon impurities are leached out to give a crystallised triarylphosphine usually having a purity of at least 95%.

When a poisoned catalyst system is taken from a hydroformylation process, it will be diluted by the presence of one or more highly volatile materials such as for example butyraldehyde. For convenience, highly volatile materials should be separated from the catalyst system before the main recovery process is begun. Separation is easily achieved by subjecting the poisoned catalyst system and its unwanted diluents to a mild evaporative separation. Suitable temperatures for the mild separation are from 150° to 300° C. and suitable pressures are from 0.01 to 0.15 MN/m$^2$. Usually temperatures of 160° to 200° C. and pressures of about atmospheric are adequate to reduce the volume of the poisoned catalyst system to a conveniently manageable size.

Evaporative separation techniques suitable for use in the performance of the main recovery process of this invention include conventional vacuum distillation, thin film evaporation and preferably wiped film evaporation.

The invention is illustrated by the following examples.

EXAMPLE 1

Propylene was hydroformylated using a conventional hydroformylation catalyst system comprising rhodium moiety and triphenylphosphine and using conventional hydroformylation conditions. Hydroformylation was continued until the reaction medium contained 0.8% by weight of poisonous n-propyldiphenylphosphine. The reaction medium containing the poisoned catalyst system was then removed from the hydroformylation reactor and subjected to a mild evaporative separation to remove highly volatile materials. The mild separation was performed in a wiped film evaporator operated at atmospheric pressure with a head temperature of from 160° to 200° C. After evaporation there remained 1350 kg of a residue containing rhodium moiety and contaminated triphenylphosphine.

The residue was then subjected to a more severe evaporative separation under reduced pressure to evaporate some of the residual volatile components (including triphenylphosphine) from the rhodium moiety. The more severe separation was performed using a wiped film evaporator operating at a head temperature of 173° C. but this time the pressure was 0.0008 MN/m$^2$. The vapour obtained was condensed forming 854 kg of condensate free from rhodium and leaving behind a residue of 351 kg which contained rhodium moiety. The condensate contained 5.42% by weight of triphenylphosphine.

In order to concentrate the triphenylphosphine, 552 kg of the condensate was passed repeatedly through the wiped film evaporator this time operated at pressures varying from 0.0005 to 0.002 MN/m$^2$ and at the milder temperatures of from 130° to 160° C. A large volume of vapour was removed and 79 kg of concentrate remained.

The concentrate was slurried with 80 kg of substantially pure methanol. The slurry was cooled to 10° C. and allowed to stand overnight. Crystals of triphenylphosphine separated out and were filtered from the concentrate. The triphenylphosphine was found to have a purity of 88%. The crystallised triphenylphosphine was then slurried for 12 hours with 80 kg of fresh pure methanol using a high energy stirrer. The triarylphosphine was filtered from the methanol and found to have a purity of 97% by weight.

The recovered triphenylphosphine was compared with fresh triphenylphosphine as a component of a conventional rhodium catalyst system in a conventional commercial process for the hydroformylation of propylene. The recovered and fresh phosphines were found to have equal selectivities and the activity of the recovered phosphine was recorded as being at least as good as than that of the fresh phosphine. In fact there was some indication that the recovered phosphine might be more active than the fresh.

EXAMPLE 2

This example illustrates the use of aqueous methanol as a polar solvent.

A condensed rhodium-free concentrate containing 11.2 g of triphenylphosphine amounting to 38.3% by weight of the concentrate was mixed with 86.5 mls of methanol and 18.5 mls of water. This mixture was cooled to 2° C. and held at that temperature for 18 hours. 4 g of re-usable cyrstalline triphenylphosphine formed and it had a purity of 93% by weight.

EXAMPLE 3

Example 2 was repeated except that the polar solvent was a mixture of 26 mls of isopropanol with 4 mls of water and the concentrate contained 10.9 g of triphenylphosphine amounting to 32.3% by weight of the concentrate. 4 g of re-usable crystalline triphenylphosphine formed and it had a purity of 88% by weight.

We claim:

1. A process for recovering triarylphosphine from a poisoned rhodium catalyst system comprising components which include rhodium moiety, triarylphosphine and poison, the process comprising separating components by evaporative and crystallisation techniques wherein the poison comprises a poisonous amount of alkyldiarylphosphine and therein the process also comprises:
   (a) subjecting the poisoned catalyst system to conditions of temperature and pressure which cause evaporative separation from the rhodium moiety of a vapour comprising triarylphosphine and material which is more volatile than triarylphosphine and then condensing the vapour,
   (b) subjecting the condensed vapour to a further but milder evaporative process which causes evaporation of at least some of the material which is more volatile than triarylphosphine so producing a concentrate of triarylphosphine and then
   (c) mixing the concentrate with a polar solvent, cooling the mixture to a temperature at which the triarylphosphine crystallises from the remainder of the mixture and recovering the crystallised triarylphosphine by physical separation from the remainder of the mixture.

2. A process according to claim 1 wherein the vapour comprising triarylphosphine is evaporatively separated from the rhodium moiety by subjecting the poisoned catalyst system to a temperature of 150° to 220° C. and to a pressure of below 0.001 MN/m$^2$.

3. A process according to claim 1 or claim 2 wherein the milder evaporative process is performed at a temperature in the range 100° to 200° C. and a pressure in the range 0.0005 to 0.1 MN/mn$^2$.

4. A process according to claim 1 wherein the polar solvent is non-acidic and miscible with water.

5. A process according to claim 4 wherein the polar solvent is an alcohol containing from 1 to 6 carbon atoms.

6. A process according to claim 4 wherein the polar solvent additionally comprises water.

7. A process according to claim 4 wherein the recovered crystalline triarylphosphine is agitated with fresh solvent whereby the purity of the triarylphosphine is increased.

8. A process according to claim 1 wherein the poisoned rhodium catalyst system is taken from the reaction medium used in a process for the hydroformylation of olefins.

9. A process according to claim 8 wherein the poisoned catalyst system is subjected to a mild evaporative separation before separation of the vapour comprising triarylphosphine from the rhodium moiety, the mild separation being performed at a temperature in the range 150° to 300° C. and a pressure not less than 0.01 $MN/m^2$ whereby highly volatile materials which dilute the catalyst system are removed.

* * * * *